United States Patent
Nagasawa et al.

(10) Patent No.: US 9,125,818 B2
(45) Date of Patent: *Sep. 8, 2015

(54) ALGINATE IMPRESSION MATERIAL FOR DENTAL USE AND CURING AGENT PASTE USED THEREFOR

(75) Inventors: Yuko Nagasawa, Tokyo (JP); Koji Matsushige, Tokyo (JP); Hidetoshi Gyakushi, Tokyo (JP)

(73) Assignee: TOKUYAMA DENTAL CORPORATION (JP)

(*) Notice: Subject to any disclaimer, the term of this patent is extended or adjusted under 35 U.S.C. 154(b) by 0 days.

This patent is subject to a terminal disclaimer.

(21) Appl. No.: 13/884,510

(22) PCT Filed: Oct. 21, 2011

(86) PCT No.: PCT/JP2011/074256
§ 371 (c)(1),
(2), (4) Date: May 9, 2013

(87) PCT Pub. No.: WO2012/063618
PCT Pub. Date: May 18, 2012

(65) Prior Publication Data
US 2013/0220172 A1    Aug. 29, 2013

(30) Foreign Application Priority Data
Nov. 10, 2010 (JP) ................. 2010-252232

(51) Int. Cl.
*A61K 6/10* (2006.01)
(52) U.S. Cl.
CPC .................... *A61K 6/10* (2013.01)
(58) Field of Classification Search
CPC .................. A61K 6/10; C08L 5/04
USPC ............................. 106/35, 205.7
See application file for complete search history.

(56) References Cited

U.S. PATENT DOCUMENTS 7,037,367 B2 * 5/2006 Mauchamp et al. ....... 106/148.1

FOREIGN PATENT DOCUMENTS

| EP | 0048123 A1 | | 3/1982 |
|----|------------|---|--------|
| EP | 0600730 A1 | | 6/1994 |
| GB | 2090272 | * | 7/1982 |
| GB | 2090272 A | | 7/1982 |
| JP | 58-35105 A | | 3/1983 |
| JP | 62-265210 A | | 11/1987 |
| JP | 10-139615 A | | 5/1998 |
| JP | 10-139616 A | | 5/1998 |
| JP | 2003-171219 A | | 6/2003 |
| JP | 2004-269385 A | | 9/2004 |
| JP | 2006-273720 A | | 10/2006 |
| WO | 2011132699 A1 | | 10/2011 |

OTHER PUBLICATIONS

International Search Report for International Application No. PCT/JP2011/074256, mailed Nov. 22, 2011, with English translation.
Extended European Search Report for the international patent application No. 11839521.-91501/2638893, dated Jul. 22, 2014.
Syed K. H. Gulrez et al. (2011), "Hydrogels: Methods of Preparation, Characterization and Applications, Progress in Molecular and Environmental Bioengineering", From Analysis and Modeling to Technology Applications, Prof. Angelo Carpi (Ed.) ISBM: 978-9536-307-268-5, In Tech, available from : http://www.intechopen.com; pp. 117-151.

* cited by examiner

*Primary Examiner* — Carol M Koslow
(74) *Attorney, Agent, or Firm* — Cantor Colburn LLP

(57) ABSTRACT

To suppress a curing agent paste stored in a sealed state in a packaging container from self-curing over a long period of time, provided are a dental alginate impression material as described below, and a curing agent paste to be used for the dental alginate impression material. The dental alginate impression material may includes: a base material paste including as main components: an alginic acid salt (A); and water (B); and a curing agent paste including as main components: a gelling reaction agent (C); a poorly water-soluble organic solvent (D); and a humectant (E).

5 Claims, 1 Drawing Sheet

ALGINATE IMPRESSION MATERIAL FOR DENTAL USE AND CURING AGENT PASTE USED THEREFOR

CROSS REFERENCE TO RELATED APPLICATIONS

This is the U.S. national stage of application No. PCT/JP2011/074256, filed on 21 Oct. 2011. Priority under 35 U.S.C. §119 (a) and 35 U.S.C. §365(b) is claimed from Japanese Application No. 2010-252232, filed 10 Nov. 2010, the disclosure of which is also incorporated herein by reference.

TECHNICAL FIELD

The present invention relates to a dental alginate impression material, and a curing agent paste to be used for the dental alginate impression material.

BACKGROUND ART

When cast crown restorative treatment, prosthodontic treatment for missing teeth, or the like is required for restoring teeth and the like, an imprint of abutment teeth and the like is taken first. Next, a model made of gypsum or the like is produced through use of the taken imprint. Then, a prosthetic appliance is produced based on the model, and the produced prosthetic appliance is attached to the abutment teeth and the like. The imprint of the abutment teeth and the like is called an impression, and a curing material for taking the impression is called an impression material. As the impression material, for example, there are used an alginate impression material, an agar impression material, a silicone rubber impression material, a polysulfide rubber impression material, and a polyether rubber impression material. Of those, an alginate impression material is most widely used because it is inexpensive and easy in handling.

There are proposals concerning various types of the alginate impression material. For example, the applicant of the present application has already proposed an alginate impression material containing an organic hydroxy compound in which a value obtained by dividing a molecular weight by the number of hydroxyl groups in a molecule is less than 40 and the number of hydroxy groups in one molecule is 3 or more, for the purpose of, for example, improving impression material properties (Patent Literatures 1 and 2). There is also a proposal concerning an alginate impression material blended with a sugar alcohol such as xylite, a sucrose fatty acid ester, or the like, in order to prevent evaporation of moisture from a cured product (Patent Literatures 3 and 4).

Work for taking an impression through use of the alginate impression material is carried out according to the following procedures. First, a product obtained by kneading constituents of the alginate impression material is mounted on an impression tray made into a similar shape to that of arrangement of teeth. Next, the tray on which the impression material is mounted is pressed against the teeth so that the tray covers the teeth in the oral cavity. Then, after the alginate impression material has been cured, an integrated product of the alginate impression material and the tray is removed from the teeth and taken out of the oral cavity.

In using the alginate impression material, main components including an alginic acid salt, a gelling reaction agent such as calcium sulfate, water, and the like are kneaded together to be used. In addition, as the alginate impression material in a state before use, in order to ensure its storage stability, there are known a powder type alginate impression material in which solid contents obtained by removing water are formed into powder and a paste type alginate impression material in which a paste containing an alginic acid salt and water as main components (base material paste) is used in combination with a paste containing a gelling reaction agent as a main component (curing agent paste). In addition, upon use, the powder and water are kneaded together in the powder type alginate impression material, and the two kinds of pastes are kneaded together in the paste type alginate impression material.

The powder type alginate impression material requires proficient skills based on handwork upon kneading work. On the other hand, in the paste type alginate impression material, automation and labor saving of kneading work can be easily achieved through use of a dedicated kneading apparatus for kneading the base material paste and the curing agent paste together. Therefore, in recent years, the paste type alginate impression material has become popular as an alternative to the powder type alginate impression material.

CITATION LIST

Patent Literature

[PTL 1] JP 2003-171219 A
[PTL 2] JP 2004-269385 A
[PTL 3] JP 10-139615 A (Claim 1, paragraph [0014], Table 1, etc.)
[PTL 4] JP 10-139616 A (Claim 1, paragraph [0016], Table 1, etc.)

SUMMARY OF INVENTION

Technical Problem

Such paste type alginate impression material is generally provided to a user such as a dentist or a dental hygienist in a form in which the base material paste and the curing agent paste are stored in a sealed state in packaging containers such as aluminum packs, respectively. In this case, upon kneading work, an opening of the packaging container for the base material paste is connected to a base material paste inlet of a kneading apparatus and an opening of the packaging container for the curing agent paste is connected to a curing agent paste inlet of the kneading apparatus. Then, in this state, the two kinds of pastes supplied from the respective packaging containers into the kneading apparatus are automatically kneaded together in the kneading apparatus. After that, the kneaded product is discharged out of the kneading apparatus. This allows the user to obtain the kneaded product. Hence, it is necessary that the pastes in the packaging containers each have appropriate fluidity so that the pastes in the packaging containers can be smoothly supplied into the kneading apparatus in performing such kneading treatment. Therefore, the pastes stored in a sealed state in the packaging containers each have a viscosity adjusted so as to have appropriate fluidity at the stage immediately after manufacture.

However, the curing agent paste undergoes a reduction in fluidity with a lapse of time, and self-cures. In addition, when the curing occurs, the curing agent paste cannot be ejected from the opening of the packaging container, which makes it impossible to utilize the curing agent paste for producing the kneaded product. That is, the expiration date of the curing agent paste stored in a sealed state in the packaging container is affected by a speed at which the self-curing progresses. As a result, the expiration date of the curing agent paste depends on the speed at which the self-curing progresses.

The present invention has been made in view of the above-mentioned circumstances. An object of the present invention is to provide a dental alginate impression material capable of suppressing a curing agent paste stored in a sealed state in a packaging container from self-curing over a long period of time, and a curing agent paste to be used for the dental alginate impression material.

Solution to Problem

The above-mentioned object is attained by the present invention described below. That is, a dental alginate impression material of the present invention includes: a base material paste including as main components: an alginic acid salt (A); and water (B); and a curing agent paste including as main components: a gelling reaction agent (C); a poorly water-soluble organic solvent (D); and a humectant (E).

In a dental alginate impression material according to one embodiment of the present invention, it is preferred that the humectant (E) include a non-reducing sugar.

In a dental alginate impression material according to another embodiment of the present invention, it is preferred that the non-reducing sugar include 2 to 10 monosaccharide molecules bonded via a glycosidic bond.

In a dental alginate impression material according to another embodiment of the present invention, it is preferred that the non-reducing sugar include a disaccharide.

In a dental alginate impression material according to another embodiment of the present invention, it is preferred that the non-reducing sugar include trehalose.

A curing agent paste for a dental alginate impression material of the present invention includes as main components: a gelling reaction agent (C); a poorly water-soluble organic solvent (D); and a humectant (E).

Advantageous Effects of Invention

According to the present invention, it is possible to provide the dental alginate impression material capable of suppressing a curing agent paste stored in a sealed state in a packaging container from self-curing over a long period of time, and the curing agent paste to be used for the dental alginate impression material.

DESCRIPTION OF EMBODIMENTS

Figure 1:
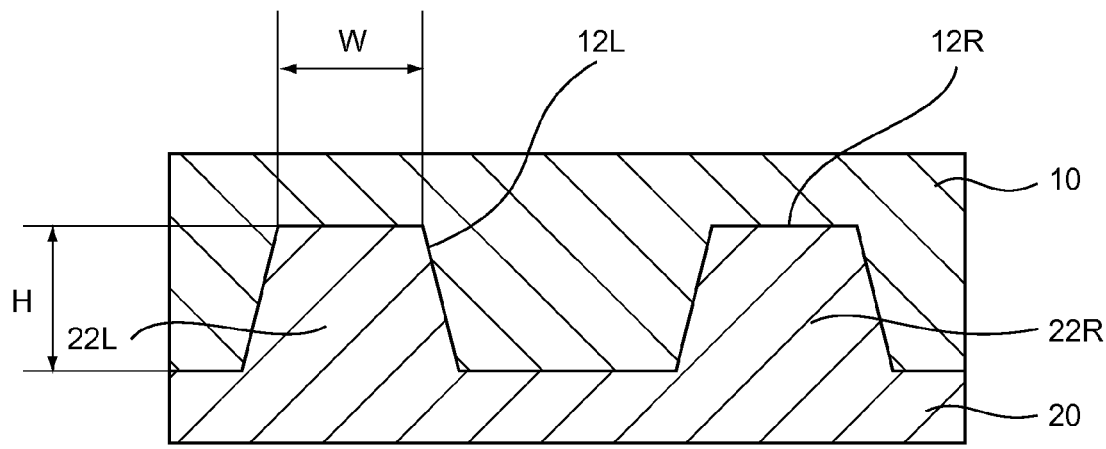
FIG. 1 A schematic view illustrating a pair of molds used in the evaluation of compatible deformation.

A dental alginate impression material (hereinafter sometimes abbreviated as "alginate impression material") according to this embodiment includes: a base material paste including as main components: an alginic acid salt (A); and water (B); and a curing agent paste including as main components: a gelling reaction agent (C); a poorly water-soluble organic solvent (D); and a humectant (E).

In the alginate impression material according to this embodiment, the curing agent paste includes the humectant (E) in addition to the gelling agent (C) and the poorly water-soluble organic solvent (D). Therefore, a curing agent paste stored in a sealed state in a packaging container can be suppressed from self-curing over a long period of time. The inventors of the present invention have estimated as described below the reasons why such effect is obtained. First, the reason why a curing agent paste stored in a sealed state in a packaging container shows an increase in viscosity with time, and self-cures is probably that a gelling reaction agent gradually reacts with moisture present in the system, which causes the curing of the gelling reaction agent. In this case, a source for the moisture present in the system is exemplified by: moisture in the ambient air which temporarily comes into contact with the curing agent paste in removing a cap for sealing an opening of the packaging container upon kneading work; crystallization water of gypsum in the case of using gypsum as the gelling reaction agent; or moisture contained in other components than the gelling reaction agent contained in the curing agent paste. However, in the alginate impression material according to this embodiment, it is considered that the humectant (E) contained in the curing agent paste absorbs the moisture present in the system, and hence a reaction between the moisture present in the system and the gelling reaction agent can be suppressed over a long period of time. That is, it is considered that the curing agent paste stored in a sealed state in a packaging container can be suppressed from self-curing over a long period of time.

It should be noted that, upon kneading work, a mixing ratio Rm of the curing agent paste to the base material paste (amount of the curing agent paste used/amount of the base material paste used (part(s) by mass/part(s) by mass)) is not particularly limited. In general, however, it is preferred that the mixing ratio Rm fall within the range of 0.25 to 1. In this case, the mixing ratio Rm may be displayed on a mixing ratio information display medium. As the mixing ratio information display medium, for example, there may be utilized: i) a product package formed of a cardboard box or the like; ii) an instruction manual for a product to be provided as a paper medium and/or electronic data; iii) a housing member (e.g., a container or a packaging bag) for storing the base material paste in a sealed state; iv) a housing member (e.g., a container or a packaging bag) for storing the curing agent paste in a sealed state; v) a product catalog to be provided as a paper medium and/or electronic data; and vi) a written message to be sent to a product user by e-mail, mail matter, or the like separately from a product. Alternatively, the mixing ratio Rm may be provided to a product user in such a mode that the mixing ratio can be recognized by the product user except the above-mentioned modes i) to vi). In this case, when a set of a housing member containing the base material paste and a housing member containing the curing agent paste, or a housing member containing any one kind of the pastes is provided to a product user, a product package and/or an instruction manual using a paper medium are/is added to those members, as necessary. Further, other additives may also be added as necessary to the curing agent paste or the base material paste. Those additives are described later. Next, constituents of the alginate impression material according to this embodiment are described.

Alginic Acid Salt (A)

Any known alginic acid salt, which is utilized in a conventional alginate impression material, may be utilized as the alginic acid salt without any particular limitation. Examples of the alginic acid salt include: i) alkali metal alginates such as sodium alginate and potassium alginate; and ii) ammonium alginates such as ammonium alginate and triethanolamine alginate. Of those alginic acid salts, an alkali metal alginate is preferably used, from the viewpoints of, for example, ease of availability, ease of handling, and physical properties of a cured product. Further, a mixture of two or more kinds of alginic acid salts may be used.

In general, the content of the alginic acid salt in a kneaded product falls within preferably the range of 2 wt % to 10 wt %. Thus, in the alginate impression material according to this embodiment, the amount of the alginic acid salt contained in the base material paste is adjusted so that the content of the alginic acid salt falls within the above-mentioned range in the kneaded product. Further, the molecular weight of the alginic acid salt is not particularly limited. In general, however, the molecular weight is preferably such a molecular weight that the viscosity of an aqueous solution containing the alginic acid salt at 1 wt % falls within the range of 50 cps to 100 cps.

Water (B)

Tap water, ion-exchanged water, distilled water, or the like may be utilized as the water. In the production of a kneaded product, the amount of the water to be used in the kneaded product falls within the range of preferably 100 parts by mass to 4,000 parts by mass, more preferably 500 parts by mass to 2,000 parts by mass, with respect to 100 parts by mass of the alginic acid salt.

Gelling Reaction Agent (C)

Any known gelling reaction agent, which is utilized in a conventional alginate impression material, may be utilized as the gelling reaction agent without any particular limitation. As the gelling reaction agent, in general, a divalent or more highly valent metal compound may be utilized. Examples thereof include i) calcium sulfate such as calcium sulfate dihydrate, calcium sulfate hemihydrate, or anhydrous calcium sulfate, ii) an oxide containing a divalent or more highly valent metal such as calcium, magnesium, zinc, aluminum, iron, titanium, zirconium, or tin, and iii) a hydroxide containing a divalent or more highly valent metal described in the item (ii). Suitable specific examples of the oxide and the hydroxide include calcium oxide, magnesium oxide, zinc oxide, titanium oxide, zirconium oxide, tin oxide, calcium hydroxide, magnesium hydroxide, zinc hydroxide, aluminum hydroxide, and iron hydroxide.

Those gelling reaction agents may be used as a mixture of two or more kinds thereof. Further, from the viewpoint that physical properties such as the curing property of a kneaded product and the elasticity of a cured product obtained by curing are made satisfactory, it is preferred to use, as the gelling reaction agent, a product obtained by blending at least one oxide selected from magnesium oxide and zinc oxide or a mixture of both the oxides in an amount within the range of 2 parts by mass to 40 parts by mass with respect to 100 parts by mass of calcium sulfate.

The blending amount of the gelling reaction agent is not particularly limited and falls within preferably the range of 10 parts by mass to 2,000 parts by mass, more preferably the range of 100 parts by mass to 1,000 parts by mass, with respect to 100 parts by mass of the alginic acid salt in the kneaded product.

It should be noted that the gelling reaction agent has a function of forming a cured product through a gelling reaction between the gelling reaction agent and the alginic acid salt in the presence of water. In this case, the water has functions of dissolving a polyvalent metal ion such as a calcium ion from the gelling reaction agent and promoting the reaction between the gelling reaction agent and the alginic acid salt, and also has a function of keeping a cured product in a gel form.

Poorly Water-Soluble Organic Solvent (D)

The poorly water-soluble organic solvent is used for the pasting of a curing agent paste containing a gelling reaction agent. That is, the poorly water-soluble organic solvent has a function of forming a paste when being mixed with a gelling reaction agent. In general, the gelling reaction agent has property of being cured through a reaction with water. Hence, in order to store the gelling reaction agent in a pasty form stably over a long period of time, a poorly water-soluble solvent which is hardly hydrated, i.e., a poorly water-soluble organic solvent is used as the solvent to be used for the pasting. Herein, the "poorly water-soluble" means that a solubility is 5 g or less in 100 g of water at a temperature of 20° C. It should be noted that the solubility of the poorly water-soluble organic solvent is preferably 3 g or less. Any known liquid may be utilized as the poorly water-soluble organic solvent as long as the liquid shows the solubility. Examples of such liquid include a hydrocarbon compound, an aliphatic alcohol, a cyclic alcohol, a fatty acid, a fatty acid salt, a fatty acid ester, and a hydrophobic polymer. Suitable examples of the various poorly water-soluble organic solvents are shown below.

First, as the hydrocarbon compound, both a chain compound and a cyclic compound may be used. Examples of the hydrocarbon compound include: aliphatic linear hydrocarbon compounds such as hexane, heptane, octane, nonane, decane, undecane, dodecane, tridecane, tetradecane, pentadecane, kerosine, 2,7-dimethyloctane, and 1-octene; alicyclic hydrocarbon compounds such as cycloheptane and cyclononane; and liquid paraffin which is a mixture of liquid saturated hydrocarbons.

Examples of the aliphatic alcohol include saturated aliphatic alcohols such as 1-hexanol and 1-octanol, and unsaturated aliphatic alcohols such as citronellol and oleyl alcohol. Examples of the cyclic alcohol include benzyl alcohol and metacresol.

Examples of the fatty acid include saturated fatty acids such as hexanoic acid and octanoic acid, and unsaturated fatty acids such as oleic acid and linoleic acid. Further, examples of the fatty acid ester include vegetable oils such as ethyl octanoate, butyl phthalate, oleic acid glyceride, olive oil, and sesame oil, and animal fats such as liver oil and whale oil. An example of the hydrophobic polymer is a polysiloxane (so-called silicone oil). Specific examples thereof include a polydimethylsiloxane, a polymethylphenylsiloxane, a polymethyl hydrogen siloxane, and a polyphenyl hydrogen siloxane.

In addition, when a manufacturing cost, living body damaging property, an influence on gustatory sensation in taking an impression of teeth, and the like are taken into consideration, it is more preferred to use a hydrocarbon compound or a hydrophobic polymer and it is particularly preferred to use liquid paraffin or silicone oil, out of the poorly water-soluble organic solvents listed in the foregoing. Further, the poorly water-soluble organic solvents may be used as a mixture of two or more kinds thereof.

The blending amount of the poorly water-soluble organic solvent is not particularly limited. In general, however, the blending amount falls within preferably the range of 10 parts by mass to 200 parts by mass, more preferably the range of 20 parts by mass to 100 parts by mass, with respect to 100 parts by mass of the gelling reaction agent.

Humectant (E)

A known substance having moisture absorbing property and moisture retaining property may be utilized as the humectant without any limitation. Suitable examples of the humectant include: an organic compound having an equilibrium moisture content of 8 wt % or more under the atmosphere of a temperature of 25° C. and a relative humidity of 90%; and a desiccant having a moisture absorptivity of 18% to 37% under the atmosphere of a temperature of 25° C. and a relative humidity of 50%. It should be noted that the equilibrium moisture content is more preferably 10 wt % or more and the moisture absorptivity is more preferably 20% to 35%. Specifically, for example, there may be used: an inorganic compound having deliquescent property such as urea, magnesium chloride, or calcium chloride; a polyhydric alcohol such as glycerin or polyethylene glycol and a polymer thereof; a cellulose-based polymer such as methylcellulose; a water absorptive polymer such as sodium polyacrylate; hyaluronic acid; collagen; and a non-reducing sugar. The blending amount of the humectant is preferably 10 parts by mass or more, more preferably 50 parts by mass or more, with respect to 100 parts by mass of the gelling reaction agent, from the viewpoint of sufficiently absorbing moisture in the system over a long period of time. It should be noted that the upper limit value of the blending amount of the humectant is not particularly limited but is preferably 500 parts by mass or less, more preferably 200 parts by mass or less, with respect to 100 parts by mass of the gelling reaction agent, from a practical viewpoint such as ensuring the blending amount of any other component. It should be noted that a non-reducing sugar is preferred among the humectants listed above.

Further, in the case of using the non-reducing sugar, the evaporation of moisture from a cured product is suppressed to a great extent. Therefore, even when the cured product is left to stand for along period of time, a reduction in impression accuracy hardly occurs. Hence, when the cured product is placed and stored in a moist box whose humidity is kept at 80% or more, a reduction in impression accuracy can be satisfactorily suppressed even after a lapse of 1 day or more from impression taking. In addition to the foregoing, there is a tendency that the cured product has a very smooth surface as compared to the case of taking an impression through use of a conventional alginate impression material, and keeps such state even when left to stand for a long period of time. Hence, an improvement in impression accuracy is also more easily achieved than ever before.

The reasons why the effects described above are obtained are estimated as described below. First, the non-reducing sugar has high affinity with a water molecule (hydration ability). Therefore, it is considered that, when the base material paste and the curing agent paste are kneaded together in order to take an impression through use of the alginate impression material according to this embodiment using the non-reducing sugar, the non-reducing sugar constitutes a molecular assembly together with a water molecule. Then, it is considered that a hydrogen bond is formed between each of alginic acid salt molecules having a hydroxy group, an ether bond, and the like and the molecular assembly by the entering of the molecular assembly between molecular chains of the alginic acid salt molecules and/or in a molecular chain of each of the alginic acid salt molecules, resulting in the strong fixation of the water molecule. That is, the water molecule is strongly fixed in a cured product containing a large amount of moisture. Therefore, the evaporation of moisture from the cured product is suppressed. As a result, it is estimated that the above-mentioned effects are obtained.

As the non-reducing sugar, a known saccharide exhibiting no reducing property may be utilized without any particular limitation. Herein, the "reducing property" means property of exhibiting a reducing action on a heavy metal ion such as a silver or copper ion in an alkaline aqueous solution. A saccharide having reducing property is detected with Tollen's reagent, Benedict's reagent, or Fehling's reagent utilizing a reducing action on a heavy metal ion. On the other hand, the non-reducing sugar which may be used in the alginate impression material according to this embodiment means a saccharide which cannot be detected with any of those reagents.

As the non-reducing sugar exhibiting the above-mentioned characteristics, there may be utilized known non-reducing sugars such as: disaccharides such as trehalose and sucrose; and oligosaccharides such as raffinose, melezitose, stachyose, and cyclodextrins. However, when the molecular weight of the non-reducing sugar is too large, the alginic acid salt and the non-reducing sugar may form a hydrogen bond to cause aggregation. Thus, from this viewpoint, as the non-reducing sugar, sugars constituted of 2 to 10 monosaccharide molecules bonded via a glycosidic bond are preferably used, and disaccharides are more preferably used. In addition, from the viewpoints of impression accuracy and moisture retaining property, trehalose is particularly preferred among the disaccharides.

The blending amount of the non-reducing sugar in the kneaded product obtained by kneading the base material paste and the curing agent paste according to the mixing ratio Rm to be provided to a product user via, for example, an instruction manual for a product falls within the range of preferably 1 part by mass to 20 parts by mass, more preferably 4 parts by mass to 12 parts by mass, with respect to 1 part by mass of the alginic acid salt. When the blending amount of the non-reducing sugar is set to 1 part by mass or more with respect to 1 part by mass of the alginic acid salt, sufficient moisture retaining property is obtained and a reduction in impression accuracy can be suppressed even when the cured product is left to stand for a longer period of time after impression taking. Further, when the blending amount of the non-reducing sugar is set to 20 parts by mass or less with respect to 1 part by mass of the alginic acid salt, the inhibition of a gelation reaction of the alginic acid salt by the non-reducing sugar upon impression taking can be suppressed.

In this case, in order that the blending amount of the non-reducing sugar in the kneaded product obtained by mixing at the mixing ratio Rm falls within the range of 1 part by mass to 20 parts by mass with respect to 1 part by mass of the alginic acid salt, a content X (wt %) of the alginic acid salt in the base material paste and a content Y (wt %) of the non-reducing sugar in the curing agent paste have only to satisfy the following expression (1).

$$X \leq Y \times Rm \leq 20 \times X \qquad \text{Expression (1)}$$

In addition, in order that the blending amount of the non-reducing sugar in the kneaded product obtained by mixing at the mixing ratio Rm falls within the range of 4 parts by mass to 12 parts by mass with respect to 1 part by mass of the alginic acid salt, the content X (wt %) of the alginic acid salt in the base material paste and the content Y (wt %) of the non-reducing sugar in the curing agent paste have only to satisfy the following expression (2).

$$4 \times X \leq Y \times Rm \leq 12 \times X \qquad \text{Expression (2)}$$

—Additive—

The alginate impression material according to this embodiment may be blended with various additives as necessary in addition to the components described above. Examples of the additive include a gelling regulator, a filler, a surfactant, an inorganic fluorine compound, an amino acid compound, an unsaturated carboxylic acid polymer, a flavor, a colorant, an antimicrobial agent, a preservative, and a pH adjustor.

It should be noted that those additives may be appropriately added to any one or both of the base material paste and the curing agent paste. However, the filler is preferably added to both of the base material paste and the curing agent paste, and the gelling regulator and the surfactant are each preferably added to the curing agent paste.

In the case of using the gelling regulator, the speed of a reaction between the alginic acid salt and the gelling reaction agent may be regulated (delayed). This makes it easy to adjust a curing time substantially in correspondence with an operation time required from the mixing/kneading of constituents of the alginate impression material to impression taking in the oral cavity in the case of a paste type or the like or an operation time required from the mixing/kneading of constituents of the alginate impression material and water to impression taking in the oral cavity in the case of a powder type or the like.

As the gelling regulator, known gelling regulators may be utilized without any limitation. Typical examples of the gelling regulator include: i) alkali metal-containing phosphoric acid salts such as trisodium phosphate, tripotassium phosphate, sodium pyrophosphate, and sodium tripolyphosphate; ii) alkali metal-containing oxalic acid salts such as sodium oxalate and potassium oxalate; and iii) alkali metal-containing carbonic acid salts such as sodium carbonate and potassium carbonate. Two or more kinds of those gelling regulators may be used as a mixture.

The blending amount of the gelling regulator may be appropriately selected depending on, for example, other blend components and a required curing time, and falls within preferably the range of 1 part by mass to 30 parts by mass, more preferably the range of 3 parts by mass to 15 parts by mass, with respect to 100 parts by weight of the alginic acid salt. The control of the blending amount of the gelling regulator within the above-mentioned range makes it easy to adjust a curing time substantially in correspondence with an operation time, and allows a cured product to be cured sufficiently.

Further, a filler is preferably used in order to adjust the physical properties of a cured product. As the filler, a clay mineral such as diatomaceous earth or talc is preferably used, and a metal or metalloid oxide such as silica or alumina may also be used. The blending amount of the filler is not particularly limited and falls within preferably the range of 50 parts by weight to 2,000 parts by mass, more preferably the range of 100 parts by mass to 1,000 parts by mass, with respect to 100 parts by mass of the alginic acid salt.

Further, for various purposes, for example, for the purposes of pasting of a gelling reaction agent component containing calcium sulfate or the like as a main component, and the like, a surfactant may also be used. Any known surfactant may be utilized as the surfactant without any particular limitation, and any of an anionic surfactant, a cationic surfactant, an amphoteric surfactant, and a nonionic surfactant may be used.

Examples of the anionic surfactant may include an alkylsulfonic acid salt, an alkylbenzenesulfonic acid salt, and an alkyl ether carboxylic acid salt. Examples of the cationic surfactant may include an alkylamine salt and a quaternary ammonium salt. The amphoteric surfactant may be, for example, an aminocarboxylic acid salt. Examples of the nonionic surfactant include a polyoxyethylene alkyl ether, a polyoxyethylene alkyl phenyl ether, a polyoxyethylene-polyoxypropylene block polymer, a polyoxyethylene glycerin fatty acid ester, a polyoxyglycerin fatty acid ester, a sorbitan fatty acid ester, a sucrose ester, a polyoxydiethylene alkylamine, and a block polymer of a polysiloxane and a polyoxyethylene.

The blending amount of the surfactant is not particularly limited and falls within preferably the range of 0.1 part by mass to 300 parts by mass, more preferably the range of 1 part by mass to 100 parts by mass, with respect to 100 parts by mass of the alginic acid salt.

Further, from the viewpoint of preventing the surface roughening of a gypsum model during impression taking or during gypsum model manufacture, it is preferred to blend an inorganic fluorine compound such as potassium titanium fluoride or potassium silicofluoride or an amino acid compound such as an amino acid/formaldehyde condensate. Further, it is preferred to blend an unsaturated carboxylic acid polymer in order to easily control the speed of a time-dependent change in viscosity of the kneaded product in the mixing/kneading of constituents of the alginate impression material in the case of a paste type or the like, or in the mixing/kneading of constituents of the alginate impression material and water in the case of a powder type or the like. Further, any one kind or a plurality of kinds of additives selected from a flavor, a colorant, a pH adjustor, an antimicrobial agent, a preservative, and the like may be blended as necessary.

—Manufacturing Method—

The base material paste and the curing agent paste for the alginate impression material according to this embodiment may be manufactured through the use of a known agitation mixer, which may be utilized in paste manufacture. In this case, examples of the agitation mixer which may be utilized include a rotating container type mixing kneader such as a ball mill, and a fixed container type mixing kneader having a horizontal axis or a vertical axis such as a ribbon mixer, a Ko-kneader, an internal mixer, a a screw kneader, a Henschel mixer, a versatile mixer, a Loedige mixer, or a butterfly mixer. Further, in the manufacture of the base material paste, when a first step of dissolving a component having relatively high solubility in water, such as a non-reducing sugar, is carried out, and then a downstream step of dissolving a component having relatively low solubility in water, such as an alginic acid salt, sequentially or collectively is carried out, there may be utilized such an agitation apparatus that no strong shearing force is applied to the component to be dissolved or a solution having the component dissolved therein in carrying out the first step. As such agitation apparatus, there may be used, for example, a transferable agitator, a vertical agitator, and a side entering agitator, equipped with various impellers, and a line agitator. In addition, in the manufacture of the base material paste and the curing agent paste, the various mixing kneaders may be utilized in combination of two or more kinds thereof.

—Use Mode of Alginate Impression Material—

In using the alginate impression material according to this embodiment, in general, at least, a kneaded product is produced from the alginate impression material according to this embodiment, and then the kneaded product is mounted on a dedicated tray. Then, the kneaded product mounted on the tray is pressed against a target such as teeth to take an impression. After that, the kneaded product after impression taking is cured to form a cured product, and then a downstream step such as a step of producing a gypsum model based on the cured product is further carried out. In this case, a known tray may be utilized as the tray without any limitation. In general, however, a tray made of a metal or a tray made of a resin is utilized. A material for the tray made of a metal is exemplified by stainless, a tin alloy, aluminum, and brass subjected to plating treatment or resin coating. It should be noted that, in the case of using the alginate impression material according to this embodiment, the kneaded product is well retained in any of the trays made of a metal. Further, a material for the tray made of a resin is exemplified by polymethacrylic acid ester.

Examples

Hereinafter, the present invention is described in more detail by way of examples. However, the present invention is by no means limited to only the following examples.

<<Abbreviated Names of Raw Materials>>

Abbreviated names of various raw materials used for the production of alginate impression materials of examples and comparative examples to be described later are as described below.

1. Gelling Reaction Agent

ZnO: zinc oxide

MgO: magnesium oxide

2. Humectant

P-Gly: polyglycerin

CaCl2: calcium chloride

3. Surfactant

Decaglyn: decaglyceryl trioleate

Gelling regulator

P3Na: trisodium phosphate

4. Filler

F1: amorphous silica having a particle diameter of 0.02 μm (methyltrichlorosilane treated product)

F2: amorphous silica having a particle diameter of 0.015 μm

5. Inorganic Fluoride

FTiK: titanium potassium fluoride

<<Evaluation Methods and Evaluation Criteria>>

An evaluation method and evaluation criteria for "ejection property" and an evaluation method for "compatible deformation" for samples of examples and comparative examples to be described later are as described below.

(1) Ejection Property

The evaluation of ejection property was carried out according to the following procedures. First, a curing agent paste immediately after production was filled into an aluminum pack equipped with a tube for ejection made of plastic having an opening with an inner diameter of 15 mm. After that, the tube for ejection was sealed with a cap made of plastic. Next, the aluminum pack into which the curing agent paste was filled in a sealed state was left to stand under a high-temperature and high-humidity environment (temperature: 50° C., humidity: 100%) for 10 days, for 30 days, and for 60 days. Then, the aluminum pack after left to stand under the high-temperature and high-humidity environment for a predetermined period of time was set in an automatic mixer for an alginate impression material AP Mixer II (manufactured by Tokuyama Dental Corporation). The curing agent paste in the aluminum pack was ejected by operating the automatic mixer for a predetermined period of time, and was measured for its ejection amount at this time. In this case, the curing agent paste in the aluminum pack stored for 0 days under the high-temperature and high-humidity environment was also ejected by operating the automatic mixer under the same conditions as in the case of using the aluminum pack stored under the high-temperature and high-humidity environment, and was measured for its ejection amount. Further, with regard to the aluminum pack used for the ejection test, the hardness of the curing agent paste filled into the aluminum pack was examined by pressing the aluminum pack by hand before the ejection test.

Then, through use of the sample stored for 0 days as a reference, each of the samples stored for 10 days, 30 days, and 60 days was evaluated for its ejection amount and curing agent paste hardness based on the following evaluation criteria. It should be noted that the ejection property shown in the table to be described later was evaluated according to the following evaluation criteria. Further, "10 days," "30 days," and "60 days" shown in the column "Ejection property" in the table to be described later mean periods of time for which the aluminum pack is stored under the high-temperature and high-humidity environment, respectively.

—Evaluation Criteria for Ejection Property—

A: None of the ejection amount and the curing agent paste hardness changes as compared to those of the sample stored for 0 days.

B: The curing agent paste hardness slightly increases and the ejection amount decreases as compared to those of the sample stored for 0 days, but no trouble occurs in kneading work using the automatic mixer.

C: The ejection amount decreases to a great extent as compared to that of the sample stored for 0 days, and hence a trouble occurs in kneading work using the automatic mixer, with the result that impression taking cannot be accurately performed.

D: The curing agent paste cannot be ejected from the aluminum pack, and thus cannot be kneaded with a base material paste.

(2) Compatible Deformation

A pair of molds illustrated in FIG. 1 were used in the evaluation of compatible deformation. In this case, as illustrated in FIG. 1, the pair of molds used in the evaluation of the compatible deformation include a first mold 10 and a second mold 20. The first mold 10 has two recessed portions 12R, 12L, and the second mold 20 has two protruded portions 22R, 22L. Further, the first mold 10 and the second mold 20 each have such dimensional accuracy that, when the first mold 10 and the second mold 20 are fitted together so that the recessed portion 12R matches the protruded portion 22R and the recessed portion 12L matches the protruded portion 22L as illustrated in FIG. 1, both the molds can be fitted together with substantially no space therebetween. It should be noted that the shape and dimension of the protruded portions 22R, 22L are determined on the assumption of the production of a bridge crown, and each of the protruded portions 22R, 22L has a height H of 10 mm and a top surface width W of 8 mm.

Next, the preliminarily prepared base material paste and curing agent paste were kneaded together through the use of an automatic alginate impression material mixer AP Mixer II (manufactured by Tokuyama Dental Corporation) to provide a kneaded product. After that, the kneaded product was poured into a tray made of a resin having such a size that the second mold 20 was able to be housed completely, and the surface was then uniformized. Then, at the time when the uniformization of the surface of the kneaded product was finished, a button of a stopwatch was pushed to start time measurement. Subsequently, after the lapse of 20 seconds, the second mold 20 was brought into contact with the kneaded product placed in the tray made of a resin under pressure, with the surface having the protruded portions 22R, 22L provided thereon down. The kneaded product was cured by being left to stand in this state for 3 minutes. After that, the second mold 20 was removed to take an impression.

Next, the cured product after the impression taking was left to stand in a moist box formed of a hermetically sealed container containing water at the bottom and kept at a humidity of 80% or more for 24 hours. Then, high strength gypsum for impression model production (NEW FUJIROCK manufactured by GC) was poured into an impression taking portion of the cured product taken out from the moist box and then left to stand for 1 hour to cure the gypsum. In addition, high strength gypsum was poured directly into the cured product after the impression taking and then left to stand for 1 hour to cure the gypsum. Thus, two kinds of gypsum models of the second mold 20 left to stand in the moist box for 0 hours and 24 hours were obtained.

Figure 2:
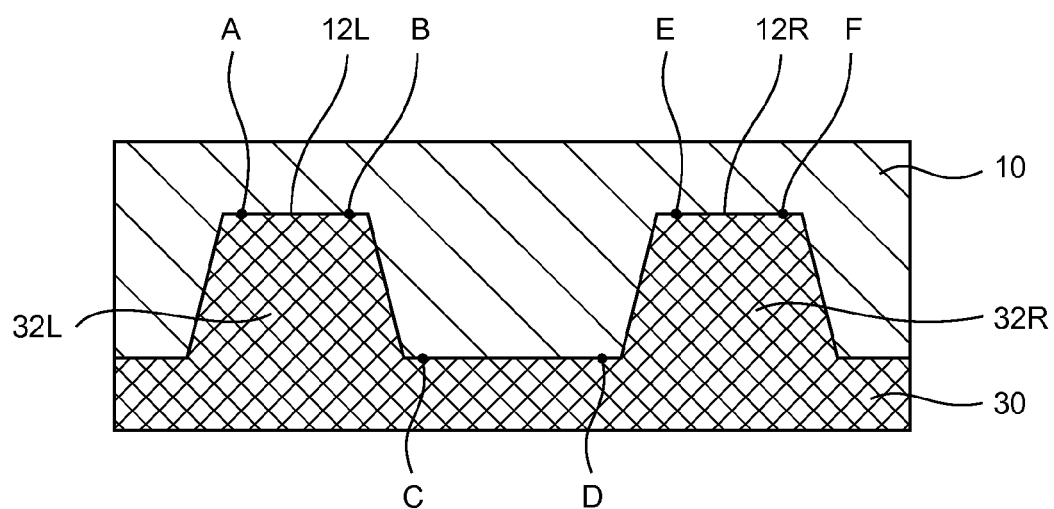
FIG. 2 A schematic view illustrating an evaluation method for compatible deformation.

After that, as illustrated in FIG. 2, in a state in which the surface of a gypsum model 30 on the side where protruded portions 32R, 32L were provided was fitted to the surface of the first mold 10 on the side where the recessed portions 12R, 12L were provided, a gap length to be formed between the gypsum model 30 and the first mold 10 was measured through the use of a microscope (laser microscope VK-8700 manufactured by KEYENCE CORPORATION). It should be noted that, as illustrated in FIG. 2, the gap length was measured at each of the following points: (1) two points in the vicinity of both the ends between the bottom surface of the recessed portion 12L and the top surface of the protruded portion 32L opposed to the bottom surface (positions represented by symbols A and B in FIG. 2); (2) two points in the vicinity of both the ends between the surface of the first mold 10 and the surface of the gypsum model 30 opposed to the surface in a region between the protruded portion 32R and the protruded portion 32L (positions represented by symbols C and D in FIG. 2); and (3) two points in the vicinity of both the ends between the bottom surface of the recessed portion 12R and the top surface of the protruded portion 32R opposed to the bottom surface (positions represented by symbols E and F in FIG. 2). Then, an average value of the six gap lengths measured at Point A to Point F was determined as "compatible deformation." It should be noted that, in FIG. 2, when the second mold 20 is used in place of the gypsum model 30, the "compatible deformation" determined in the same manner as in the case described above is 5 μm.

Further, "Immediately after" shown in the "Compatible deformation" column in the table to be described later shows the results in the case where the gypsum model 30 was produced through the use of the cured product immediately after curing (cured product stored in the moist box for 0 minutes). Further, "After 24 hours" shown in the "Compatible deformation" column in the table to be described later shows the results in the case where the gypsum model 30 was produced through the use of the resultant cured product after the cured product had been stored in the moist box for 24 hours.

Example 1

10 g of dihydrated gypsum as a gelling reaction agent (a), 5 g of hexane as a poorly water-soluble organic solvent (b), and 10 g of CaCl2 as a humectant (c) were weighed and kneaded together through use of a small kneader for 1 hour to prepare a curing agent paste. In addition, 25 g of potassium alginate as an alginic acid salt, 375 g of distilled water as water, and 88 g of diatomaceous earth as a filler were weighed and kneaded together through use of a small kneader for 1 hour to prepare a base material paste. Then, the resultant curing agent paste was evaluated for its ejection property. Further, the curing agent paste and the base material paste were kneaded together through use of an automatic mixer for an alginate impression material AP Mixer II. The kneaded product was used to perform the evaluation of compatible deformation. It should be noted that the mixing ratio Rm of the curing agent paste to the base material paste in the production of the kneaded product was set to 0.36.

Examples 2 to 18 and Comparative Examples 1 to 5

Kneaded products were each obtained by preparing a base material paste and a curing agent paste and kneading the pastes together in the same manner as in Example 1 except that the composition of the curing agent paste was changed to one shown in Table 1. Then, each of the resultant kneaded products was evaluated for its ejection property and compatible deformation in the same manner as in Example 1.

(Evaluation Results)

Table 1 shows the compositions of the curing agent pastes of Example 1 to Example 18 and Comparative Example 1 to Comparative Example 5. Further, Table 2 shows the evaluation results of the samples of Example 1 to Example 18 and Comparative Example 1 to Comparative Example 5 for ejection property and compatible deformation.

TABLE 1

| | Curing agent paste composition (parts by mass) | | | | | | | | | | | | | | |
|---|---|---|---|---|---|---|---|---|---|---|---|---|---|---|---|
| | Component a | | | | Component b Poorly water-soluble organic solvent | | Component c | | | | Other components | | | | |
| | Gelling reaction agent | | | | | | Humectant | | | | Surfactant | Gelling regulator | Filler | | Inorganic fluoride |
| | Dihydrated gypsum | Anhydrous gypsum | MgO | ZnO | Hexane | Liquid paraffin | CaCl2 | P-Gly | Sucrose | Trehalose | Decaglyn | P3Na | F1 | F2 | FTiK |
| Example 1 | 100 | — | — | — | 50 | — | 100 | — | — | — | — | — | — | — | — |
| Example 2 | 100 | — | — | — | 50 | — | — | 100 | — | — | — | — | — | — | — |
| Example 3 | 100 | — | — | — | 50 | — | — | — | 100 | — | — | — | — | — | — |
| Example 4 | 100 | — | — | — | 50 | — | — | — | — | 100 | — | — | — | — | — |
| Example 5 | 25 | 75 | — | — | 50 | — | — | — | — | 100 | — | — | — | — | — |
| Example 6 | 20 | 60 | 8 | 12 | 50 | — | — | — | — | 100 | — | — | — | — | — |
| Example 7 | 20 | 60 | 8 | 12 | — | 50 | — | — | — | 100 | — | — | — | — | — |
| Example 8 | 20 | 60 | 8 | 12 | — | 50 | — | — | — | 100 | 8 | 2 | 13 | 6 | 10 |
| Example 9 | 20 | 60 | 8 | 12 | — | 50 | — | — | — | 60 | 8 | 2 | 13 | 6 | 10 |
| Example 10 | 20 | 60 | 8 | 12 | — | 50 | — | — | — | 150 | 8 | 2 | 13 | 6 | 10 |
| Example 11 | 20 | 60 | 8 | 12 | — | 50 | 100 | — | — | — | 8 | 2 | 13 | 6 | 10 |
| Example 12 | 100 | — | — | — | 50 | — | — | — | — | 200 | — | — | — | — | — |
| Example 13 | 100 | — | — | — | 50 | — | — | — | — | 50 | — | — | — | — | — |
| Example 14 | 100 | — | — | — | 50 | — | — | — | — | 10 | — | — | — | — | — |
| Example 15 | 100 | — | — | — | 50 | — | 10 | — | — | — | — | — | — | — | — |
| Example 16 | 100 | — | — | — | 200 | — | — | — | — | 100 | — | — | — | — | — |
| Example 17 | 100 | — | — | — | 20 | — | — | — | — | 100 | — | — | — | — | — |
| Example 18 | 100 | — | — | — | 10 | — | — | — | — | 100 | — | — | — | — | — |

TABLE 1-continued

| | Curing agent paste composition (parts by mass) | | | | | | | | | | | | | |
|---|---|---|---|---|---|---|---|---|---|---|---|---|---|---|
| | Component a Gelling reaction agent | | | | Component b Poorly water-soluble organic solvent | | Component c Humectant | | | | Other components | | | |
| | | | | | | | | | | | Surfactant | Gelling regulator | Filler | Inorganic fluoride |
| | Dihydrated gypsum | Anhydrous gypsum | MgO | ZnO | Hexane | Liquid paraffin | CaCl2 | P-Gly | Sucrose | Trehalose | Decaglyn | P3Na | F1 F2 | FTiK |
| Comparative Example 1 | 100 | — | — | — | 50 | — | — | — | — | — | — | — | — — | — |
| Comparative Example 2 | 25 | 75 | — | — | 50 | — | — | — | — | — | — | — | — — | — |
| Comparative Example 3 | 20 | 60 | 8 | 12 | 50 | — | — | — | — | — | — | — | — — | — |
| Comparative Example 4 | 20 | 60 | 8 | 12 | — | 50 | — | — | — | — | — | — | — — | — |
| Comparative Example 5 | 20 | 60 | 8 | 12 | — | 50 | — | — | — | — | 8 | 2 | 13 6 | 10 |

TABLE 2

| | Ejection property | | | Compatible deformation/μm | |
|---|---|---|---|---|---|
| | | | | Immediately after | After 24 hours |
| | 10 days | 30 days | 60 days | | |
| Example 1 | B | B | C | 355 | 2,232 |
| Example 2 | B | B | C | 345 | 2,213 |
| Example 3 | A | A | B | 342 | 895 |
| Example 4 | A | A | B | 334 | 612 |
| Example 5 | A | A | B | 296 | 595 |
| Example 6 | A | A | B | 210 | 523 |
| Example 7 | A | A | B | 206 | 520 |
| Example 8 | A | A | B | 108 | 327 |
| Example 9 | A | A | B | 110 | 332 |
| Example 10 | A | A | B | 111 | 322 |
| Example 11 | A | A | B | 296 | 1,915 |
| Example 12 | A | A | B | 343 | 638 |
| Example 13 | A | A | B | 340 | 642 |
| Example 14 | B | B | C | 345 | 698 |
| Example 15 | B | C | D | 354 | 2,307 |
| Example 16 | A | A | B | 355 | 639 |
| Example 17 | A | A | B | 351 | 645 |
| Example 18 | B | C | D | 360 | 710 |
| Comparative Example 1 | D | — | — | 363 | 2,655 |
| Comparative Example 2 | D | — | — | 358 | 2,638 |
| Comparative Example 3 | D | — | — | 350 | 2,574 |
| Comparative Example 4 | D | — | — | 352 | 2,560 |
| Comparative Example 5 | D | — | — | 348 | 2,443 |

A time-dependent increase in viscosity (curing progression) of the curing agent paste was suppressed in each of Example 1 to Example 18 as compared to each of Comparative Examples 1 to 5 in which no humectant was blended. In addition to the foregoing, the curing agent paste was able to be used without any problem even after stored under the environment of a humidity of 100% and a temperature of 50° C. for 10 days in each of Example 1 to Example 18.

In addition, in the case of using, in particular, trehalose as the humectant like each of Example 4 to Example 10, Example 12 to Example 14, and Example 16 to Example 18, it was found that a time-dependent increase in viscosity (curing progression) of the curing agent paste was suppressed, and besides, the evaluation results of compatible deformation immediately after impression taking and compatible deformation after leaving to stand for 24 hours were satisfactory.

On the other hand, in each of Comparative Example 1 to Comparative Example 5 in which no humectant was blended, the curing agent paste showed a remarkable time-dependent increase in viscosity (curing progression) after stored under the environment of a humidity of 100% and a temperature of 50° C. for 10 days, and hence the curing agent paste was not able to be ejected from the aluminum pack through use of the automatic mixer.

The invention claimed is:

1. A dental alginate impression material, comprising a cured product which is obtained by mixing and kneading a base material paste with a curing agent paste, wherein:
   the base material paste comprising as main components:
      an alginic acid salt (A); and
      water (B); and
   the curing agent paste comprising as main components:
      a gelling reaction agent (C);
      a poorly water-soluble organic solvent (D); and
      a non-reducing sugar (E).

2. A dental alginate impression material according to claim 1, wherein
   the non-reducing sugar comprises 2 to 10 monosaccharide molecules bonded via a glycosidic bond.

3. A dental alginate impression material according to claim 1, wherein
   the non-reducing sugar comprises a disaccharide.

4. A dental alginate impression material according to claim 1, wherein
   the non-reducing sugar comprises trehalose.

5. A method of taking a dental impression comprising:
   providing a base material paste comprising an alginic acid salt (A), and water (B);
   providing a curing agent paste comprising a gelling reaction agent (C), a poorly water-soluble organic solvent (D), and a non-reducing sugar (E);
   preparing a kneaded product by mixing and kneading the base material paste with the curing agent paste;
   mounting the kneaded product on a tray;
   pressing the tray against a dental target to obtain the dental impression on the kneaded product.

* * * * *